United States Patent [19]

Leveskis

[11] Patent Number: 4,512,337
[45] Date of Patent: Apr. 23, 1985

[54] METHODS FOR CRYOPRESERVATION AND TRANSFER OF BOVINE EMBRYOS

[76] Inventor: Newton G. Leveskis, 8500 Mt. Vernon Rd., Auburn, Calif. 95603

[21] Appl. No.: 313,118

[22] Filed: Oct. 20, 1981

[51] Int. Cl.³ .......................... A61D 7/00; A61D 7/02
[52] U.S. Cl. .................................................... 128/1 R
[58] Field of Search ...................................... 128/1 R

[56] References Cited

U.S. PATENT DOCUMENTS

| | | | |
|---|---|---|---|
| 3,303,662 | 2/1967 | Moline et al. | 62/62 |
| 3,677,024 | 7/1972 | Segall | 62/64 |
| 3,925,903 | 12/1975 | Ward | 34/9 |
| 4,155,331 | 5/1979 | Lawrence et al. | 119/2 |
| 4,380,997 | 4/1983 | Leibo | 128/1 R |

OTHER PUBLICATIONS

Maurer, Ralph R., "Freezing Mammalian Embryos: A Review of the Techniques," *Theriogenology*, vol. 9, No. 1, Jan. 1978, pp. 45-68.
Schneider, H. J., Jr., "Cryopreservation–A New Dimension in Embryo Transfer," BULL-O-GRAM, Dec. 1979/Jan. 1980, pp. 26-30.
Baker, Robert D., "Subzero Preservation of Mammalian Embryos," International Embryo Transfer Society, Annual Conference Proceedings, 1976, 1977, Denver, Colorado.
Seidel, G. E., Jr., et al., "Bovine Embryo Transfer Procedures," Colorado State Univ., Animal Reproduction Laboratory, General Series 975, Revised Jun. 1980.
Brotman, Harris, "Freeze-Thaw Technique for Embryos," *Genetic Engineering News*, vol. 1, No. 4, Jul.-/Aug. 1981, p. 1.

*Primary Examiner*—George F. Lesmes
*Assistant Examiner*—Nancy A. B. Swisher
*Attorney, Agent, or Firm*—Townsend & Townsend

[57] ABSTRACT

Dimethyl sulfoxide is added to a solution containing a bovine embryo, and the solution including the embryo and the dimethyl sulfoxide is introduced into the uterus of a recipient animal when the recipient animal is apparently receptive to pregnancy. The dimethyl sulfoxide does not adversely affect the cells of the embryo but improves chances for a successful transplant. The dimethyl sulfoxide is added directly to the solution containing the bovine embryo until the desired final concentration (usually about 1.5M) is present therein. When the embryo is frozen to preserve it prior to transfer to a recipient animal, the freezing can be more rapidly accomplished. The solution containing the embryo is cooled at a rate of about 1° C. per minute until the solution temperature is about −7° C., the solution is then seeded, and then the solution temperature is lowered about 1° C. per minute until reaching about −30° C., at which point the solution is plunged into liquid nitrogen.

10 Claims, No Drawings

METHODS FOR CRYOPRESERVATION AND TRANSFER OF BOVINE EMBRYOS

BACKGROUND OF THE INVENTION

1. Field of the Invention

This invention relates to the transfer of a bovine embryo from a donor cow to a recipient cow. In a preferred embodiment the invention relates to freezing the embryo to preserve it between the time of collection from the donor and implantation in the recipient.

2. Brief Description of the Prior Art

In recent years embryo transfer in cattle has grown rapidly to become a viable component of the animal industry. The primary purpose of embryo transfer is to increase the reproductive capacity of valuable females. With the technique it is possible to utilize genetically superior females, obtain a large number of embryos from them with the techniques of superovulation and artificial insemination, and then disseminate the embryos to other parts of the country and of the world where they can be implanted in local female recipients.

The entire process is optimized when the embryos are rendered in a form suitable for storage. To this end freezing has been utilized. The frozen embryos can be transported over longer distances and into less accessible regions than has been possible with the non-frozen embryos. The transfer of embryos and the use of freezing to render them storable will help to increase animal production. Being able to store the embryos in a state of animation will also greatly facilitate the timing between embryo production and receptivity of the recipient animals.

The practices to date in connection with freezing of embryos have utilized a relatively slow procedure in reducing temperature as a precaution against damaging the cells of the embryo by the freezing process. Typically, temperature reduction has proceeded at the rate of about 1° C. per minute until the embryo reached about −6° C. to −7° C., at which point seeding was executed. Thereafter temperature reduction was limited to a fraction of a degree, such as about 0.3° C. per minute, until the temperature was lowered to about −30° C. Further reduction to about −33° C. was even more slowly executed at a rate of about 0.1° C. per minute, at which time the embryo was plunged into liquid nitrogen. See, for example, "Freezing Mammalian Embryos: A Review of the Techniques", Ralph R. Maurer, *Theriogenology*, Vol. 9, No. 1, January 1978, pp. 45–68, and in particular, page 58.

It has also been known to use a cryoprotective agent such as dimethyl sulfoxide. Again, in order to avoid adverse affect on the cells of the embryo, particularly osmotic shock which might rupture the cell walls or internal cellular structures, the cryoprotective agent was added through a series of solutions with the embryo being transferred from solution to solution containing increasingly higher concentrations of the cryoprotective agent. Again, the procedure has been time consuming and laborious. Finally, for similar reasons it was thought necessary to remove the cryoprotective agent, such as dimethyl sulfoxide, after thawing the frozen embryo and before implanting it in the recipient animal. The removal was again executed with a series of solutions containing progressively more dilute concentrations of the cryoprotective agent.

SUMMARY OF THE INVENTION

The present invention greatly simplifies the prior procedures for cooling and adding cryoprotective agents. It has been found that cooling can be more rapidly executed without adversely affecting the viability of embryos. In addition, it has been found that the dimethyl sulfoxide can be added directly to the initial solution containing the embryo until the final desired concentration is present in the initial solution. Serial transfer to solutions of increasingly higher concentration is found to be unnecessary.

Of great significance, it has been found that the dimethyl sulfoxide need not be removed from the embryotic solution prior to transplantation and after thawing. Most surprisingly, it is found that no adverse affects on the success of the transplant occur. Rather, it appears that the presence of the dimethyl sulfoxide in the recipient uterus is beneficial. It is believed that the dimethyl sulfoxide aids in anchoring the embryo in the recipient uterus and promotes the desired physiological interconnection of the embryo thereto.

More particularly, the present invention provides a method for transferring a bovine embryo comprising: providing a bovine embryo in a physiologically buffered solution, said solution containing a cryoprotective amount of dimethyl sulfoxide, and moving said solution containing the embryo and substantially all of said dimethyl sulfoxide into the uterus of a recipient bovine animal when the animal is apparently receptive to pregnancy. In the usual case, the dimethyl sulfoxide is present in a concentration of about 1.5M in said buffered solution, with the buffered solution being a phosphate buffered saline solution. Where the embryo is first frozen and thereafter thawed before being moved into the uterus of the recipient animal, freezing is accomplished by lowering the temperature of the buffered solution containing the embryo at a rate of about 1° C. per minute until the solution temperature is about −7° C., then seeding the solution, thereafter lowering the solution temperature about 1° C. per minute until its temperature is about −30° C., and then plunging the solution into liquid nitrogen.

As noted above, the dimethyl sulfoxide can be added directly to the initial solution containing the embryo, whether or not the embryo is to be frozen. The dimethyl sulfoxide is added in a cryoprotective amount of about 1–2M, usually in a concentration of about 1.5M. The dimethyl sulfoxide is added at a relatively slow rate, preferably so as to result in a change per minute of about 0.06–0.07M.

DESCRIPTION OF THE PREFERRED EMBODIMENT

A simmental cow was superovulated with a series of appropriate injections and thereafter artificially inseminated. The fertilized ova were collected non-surgically the next day and frozen with the following procedure.

Each embryo was placed in a phosphate saline buffer (Gibco PBS). Dimethyl sulfoxide was slowly added over a period of thirty-five minutes. During this time 1 cc of dimethyl sulfoxide was added to 9 cc of the phosphate buffer with slight agitation. A plastic straw (0.5 cc volume) was utilized for each embryo. The straw had a permanent plug at one end and into it was placed a small quantity of the buffer, then the embryo and then some additional buffer. A removable plastic plug was inserted in the other end of the straw.

The straw was then placed in a bath of isopropyl alcohol and a lead foil was used on the end of the straw with the plastic plug to keep the straw submerged in the isopropyl alcohol. Liquid nitrogen was poured into the isopropyl alcohol so as to cool the bath at the rate of 1° C. per minute until reaching −7° C. The straw was then seeded. Seeding can be accomplished by adding a crystal of sterile ice to the straw, or by touching the exterior of the straw with an instrument which has been cooled in liquid nitrogen. After seeding the bath wass cooled at the rate of 1° C. per minute until it reached −30° C., whereafter the straw was plunged into liquid nitrogen and stored in a tank containing liquid nitrogen.

Approximately two weeks later the frozen embryos were thawed by placing the straws in water at 25° C. The removable plug end may have to be held closed during the thawing process, or internal pressure may cause the contents to be prematurely pushed out of the straw. The plastic plug end of the straw was clipped and the straw was placed in a sterilized straw insemination gun. A sterilized drinking straw with one end closed was used as a protective cover over the loaded insemination gun. The thawed embryo was inserted in the upper third of one horn of the uterus of a shorthorn cow seven and one-half days after she was in heat. The inserted solution containing the thawed embryo still contained the dimethyl sulfoxide which had been added prior to freezing.

Approximately five months later the cow receiving the implanted embryo was examined by palpation of the uterus. It was determined that the cow was pregnant.

A number of embryos have been frozen, thawed and implanted using the above techniques. The number of successful pregnancies existing three months after transplantation has been about sixty percent of the total embryos for which transplantation has been attempted.

I claim:

1. A method for transferring a bovine embryo comprising:
providing a bovine embryo in a physiologically buffered solution, said solution containing a cryoprotective amount of dimethyl sulfoxide, and moving said solution containing the embryo and substantially all of said dimethyl sulfoxide without additional dilution into the uterus of a recipient bovine animal when the animal is apparently receptive to pregnancy.

2. The method in accordance with claim 1 wherein the dimethyl sulfoxide is present in a concentration of about 1.5M in said buffered solution.

3. The method in accordance with claim 2 wherein said solution containing the embryo is first frozen and thereafter thawed before being moved into the uterus of said recipient animal.

4. The method in accordance with claim 3 wherein said embryo is frozen by lowering the temperature of the buffered solution containing the embryo at a rate of about 1° C. per minute until the solution temperature is about −7° C., then seeding the solution, thereafter lowering the solution temperature about 1° C. per minute until its temperature is about −30° C., and then plunging the solution into liquid nitrogen.

5. A method for freezing a bovine embryo comprising:
providing a bovine embryo in an initial buffered solution, adding dimethyl sulfoxide at a preselected single concentration within the range of 1-2M'', slowly and substantially continuously at a constant rate per minute to said solution until a cryoprotective amount is present therein, and lowering the temperature of said solution sufficiently to preserve the embryo in a viable condition.

6. A method in accordance with claim 5 wherein the dimethyl sulfoxide is added to said initial solution to provide a final concentration of about 1.5M.

7. A method in accordance with claim 6 wherein said dimethyl sulfoxide is added at a rate to provide about a 0.06-0.07M change per minute.

8. A method in accordance with claim 5 wherein said temperature is lowered by placing the buffered solution containing the embryo and dimethyl sulfoxide in an external alcohol bath and lowering the temperature of the alcohol bath.

9. A method in accordance with claim 8 wherein the temperature of the alcohol bath is lowered by adding liquid nitrogen thereto.

10. A method in accordance with claims 5 or 8 wherein the alcohol bath is lowered about 1° C. per minute to a temperature of about −7° C., the buffered solution is then seeded, then the alcohol bath is lowered in temperature about 1° C. per minute until reaching about −30° C., and then the buffered solution containing the embryo and dimethyl sulfoxide is plunged into liquid nitrogen.

* * * * *